United States Patent [19]
Leet et al.

[11] Patent Number: 6,153,792
[45] Date of Patent: Nov. 28, 2000

[54] CARBONYLATION PROCESS USING A FLASH STEP WITH WASHING

[75] Inventors: William A. Leet, Naperville; Santi Kulprathipanja, Inverness, both of Ill.

[73] Assignee: UOP LLC, Des Plaines, Ill.

[21] Appl. No.: 09/216,399

[22] Filed: Dec. 18, 1998

Related U.S. Application Data

[60] Provisional application No. 60/068,024, Dec. 18, 1997.

[51] Int. Cl.[7] ............................ C07C 51/12; C07C 51/10; C07C 51/14; C07C 67/00
[52] U.S. Cl. .......................... 562/519; 562/517; 562/520; 560/204
[58] Field of Search .................................. 562/517, 519, 562/520; 560/204

[56] References Cited

U.S. PATENT DOCUMENTS

| | | | |
|---|---|---|---|
| 3,769,329 | 10/1973 | Paulik et al. | 260/488 K |
| 3,791,935 | 2/1974 | Eubanks et al. | 203/74 |
| 5,227,520 | 7/1993 | Cooper | 562/519 |
| 5,334,755 | 8/1994 | Yoneda et al. | 562/519 |
| 5,364,963 | 11/1994 | Minami et al. | 562/519 |
| 5,374,774 | 12/1994 | Ochiai | 562/519 |
| 5,466,874 | 11/1995 | Scates et al. | 562/519 |
| 5,520,890 | 5/1996 | Lorentzen et al. | 422/197 |
| 5,662,780 | 9/1997 | Sasaki et al. | 203/81 |
| 5,663,430 | 9/1997 | Morris et al. | 562/608 |

FOREIGN PATENT DOCUMENTS 0 846 674 A1  6/1998  European Pat. Off. ........ C07C 51/12

OTHER PUBLICATIONS

Acetic Acid and Derivatives pp. 121–139 *Kirk–Othmer Encyclopedia of Chemical Technology*, 4th Edition, vol. 1, John Wiley and Sons, New York, 1991.

The Chiyoda/UOP Acetica™ Process: A Novel Acetic Acid Technology by Noriyuki Yoneda et al. presented at Third Annual Tokyo Conference on Advanced Catalytic Science and Technology Japan 1998.

"Acetic Acid by Low Pressure Carbonylation of Metanol with a Supported Rhodium Catalyst" by Wing S. Fong, Process Economics Program, PEP Review No. 88–3–4, SRI International, Menlo Park, CA, Feb. (1990), pp. 1–14.

*Primary Examiner*—Johann Richter
*Assistant Examiner*—J. Parsa
*Attorney, Agent, or Firm*—John G. Tolomei; Michael A. Moore

[57] ABSTRACT

A process for the production of a carboxylic acid in the presence of solid catalyst particles that employs a flash step with a liquid wash is disclosed. This process helps prevent the buildup of deposits of solid catalyst particles, attrited solid catalyst particles, and heavy by-products in the flash zone. This invention is useful for the production of carboxylic acids, especially acetic acid.

21 Claims, 1 Drawing Sheet

CARBONYLATION PROCESS USING A FLASH STEP WITH WASHING

CROSS-REFERENCE TO RELATED APPLICATION

This application claims the benefit of U.S. Provisional Application Ser. No. 60/068,024, filed on Dec. 18, 1997.

FIELD OF THE INVENTION

This invention generally relates to producing carboxylic acids with less fouling of equipment. Specifically, this invention relates to a method of reducing or eliminating fouling in a process for producing carboxylic acids using a heterogeneous catalyst.

BACKGROUND OF THE INVENTION

The production of carboxylic acids by the carbonylation of alcohols with carbon monoxide is well known. One example, the carbonylation of methanol, is the most important reaction for the commercial production of acetic acid. Acetic acid, which is a principal ingredient in vinegar, has hundreds of uses in addition to giving flavor to cooking and salads. Paints and adhesives contain latex emulsion resins polymerized from vinyl acetate monomer (VAM) made with acetic acid, and some cellulosic fibers and plastics are manufactured from acetic anhydride derived from acetic acid.

Both homogeneous and heterogeneous catalysts for the carbonylation of methanol to acetic acid are known. Although homogeneous catalysts are well known, they cause numerous problems. U.S. Pat. No. 5,334,755 (Yoneda et al.) lists the problems associated with a homogeneous rhodium compound-methyl iodide catalyst dissolved in acetic acid, including primarily that overly large reactors and reactor-related equipment are needed due to the low solubility of the rhodium compound in acetic acid. Other problems with homogeneous catalysts include that operating costs are relatively high when low water levels are employed and excessive hydrogen iodide corrosion occurs when high water levels are used. Heterogeneous catalysts, on the other hand, have as a primary advantage over homogeneous catalysts the fact that smaller reactors can be used. Heterogeneous catalysts are disclosed in U.S. Pat. No. 4,328,125 (Drago et al.); U.S. Pat. No. 5,155,261 (Marston et al.); U.S. Pat. No. 5,281,359 (Scates et al.); U.S. Pat. No. 5,334,755 (Yoneda et al.); U.S. Pat. No. 5,364,963 (Minami et al.); and U.S. Pat. No. 5,466,874 (Scates et al.).

One of the problems with heterogeneous catalysts is that a heterogeneous catalyst can exit the reaction zone with the reaction effluent and settle out or otherwise accumulate in downstream equipment. Another problem with heterogeneous catalysts is that a heterogeneous catalyst can undergo some attrition during its useful life in catalyzing carbonylation reactions. To clarify, it is helpful to define the term "attrited solid catalyst particles" as used herein. "Attrited solid catalyst particles" means solid catalyst particles that have undergone mechanical attrition and/or thermal attrition. Mechanical attrition means the transformation of larger catalyst particles into smaller catalyst particles in the absence of a change in the chemical composition of the catalyst particles. Examples of mechanical attrition include breakage and fracturing, which can yield chips, pieces, fines, or other fragments of the solid catalyst particles. Most commonly, mechanical attrition of catalyst particles occurs during transport or other movement of the catalyst particles. Transport of the catalyst particles subjects the catalyst particles to erosion and abrasion as a result of contact with other catalyst particles as well as with the inner surfaces and edges of vessels and conduits.

Thermal attrition means the transformation of catalyst particles that occurs as a result of exposure to elevated temperature and that does result in a change in the chemical composition of the catalyst particles. Polyvinylpyridine resin, which is a common carbonylation catalyst, serves to illustrate two examples of thermal attrition, namely first the breakdown of the cross-linkages within the polyvinylpyridine resin, and second the breakdown of the linkages comprising the backbone of the polyvinylpyridine resin. It should be pointed out, however, that the term "thermal attrition," in the case of resins, is meant to exclude the plasticization or melting of the resin, the decomposition of the resin into a gum, the decomposition of the resin into a soft coke, and the complete depolymerization of the resin. Although polyvinylpyridine resins at certain conditions can melt and can undergo such decomposition and complete depolymerization reactions, these reactions are deleterious to the select properties of the polyvinylpyridine resins to catalyze carbonylation, and therefore carbonylation processes are generally operated outside the range of conditions at which such decomposition and depolymerization reactions occur.

The problem with attrited solid catalyst particles is that attrited solid catalyst particles tend to severely foul equipment in which the phase of the bulk fluid that carries the attrited solid catalyst particles changes from a liquid to vapor. When a liquid-solid reaction effluent that contains attrited solid catalyst particles flows through equipment such as flash drums and heat exchangers wherein the liquid phase is at least partially vaporized, the attrited solid catalyst particles can cluster or settle and compress into deposits which are difficult to remove or which with heat input can form a tar-like deposit. Such deposits can interfere with the performance of this equipment. Solid catalyst particles, in turn, can stick or adhere to the tar-like deposit, thereby adding to the quantity of the deposits.

Tar-like deposits can become even more problematic when the attrited solid catalyst particles combine with heavy by-products of side reactions that occur during carbonylation. As used herein, the term "heavy by-product" means a product of the reaction zone that has one more carbon atom than that of the desired carboxylic acid product. In the production of acetic acid, for example, propionic acid and other compounds having three or more carbon atoms are considered to be heavy by-products. Generally, at separation conditions, a heavy by-product has a boiling point that is greater than that of the desired carboxylic acid product. Thus, at normal conditions, propionic acid boils at about 141° C. while acetic acid boils at 118° C. Of course, even in the absence of attrited solid catalyst particles, heavy by-products alone can foul or otherwise interfere with the operation of downstream equipment.

Accordingly, methods are sought that prevent or at least alleviate the fouling problems that can arise as a result of the use of heterogeneous catalysts in carbonylation processes, in order that the benefits associated with the use of heterogeneous catalysts can be more fully realized.

SUMMARY OF THE INVENTION

This invention is a process for the production of a carboxylic acid in the presence of solid catalyst particles that employs a flash step with a liquid wash. This invention helps prevent the buildup of deposits of solid catalyst particles, attrited solid catalyst particles, and heavy by-products in the flash zone.

Accordingly, this invention is a process for the production of a carboxylic acid. An alcohol and/or a reactive derivative of an alcohol is reacted with carbon monoxide in the presence of solid catalyst particles in a reaction zone to produce a carboxylic acid. A reaction effluent is withdrawn from the reaction zone. The reaction effluent comprises carboxylic acid and at least one of solid catalyst particles, attrited solid catalyst particles, and heavy by-products. At least a portion of the reaction effluent is flashed in a flash zone. An overhead stream comprising carboxylic acid is recovered from the flash zone. A first portion of the overhead stream is recycled to the flash zone. The first portion of the overhead stream is at least partially in the liquid phase. Carboxylic acid is recovered from a second portion of the overhead stream.

In another embodiment, this invention is a process for the production of a carboxylic acid. An alcohol and/or a reactive derivative of an alcohol is reacted with carbon monoxide in the presence of solid catalyst particles in a reaction zone to produce carboxylic acids. A reaction effluent is withdrawn from the reaction zone. The reaction effluent comprises carbon monoxide, water, esters corresponding to the esterification of the alcohol and carboxylic acids, carboxylic acids, and at least one of the group consisting of solid catalyst particles, attrited solid catalyst particles, and heavy by-products. The esters comprise a light ester having a boiling point less than the carboxylic acids. The reaction effluent is flashed in a vertically-oriented flash zone. The flash zone has a rectification section in an upper portion of the flash zone and a packed section in a lower portion of the flash zone. The packed section contains packing. A vapor stream comprising carbon monoxide, water, and the light ester is withdrawn from the flash zone at a point above the top of the rectification section. A liquid stream comprising carboxylic acid is withdrawn from the flash zone at a point below the top of rectification section and above the top of the packed section. A bottom stream comprising carboxylic acid and at least one of the group consisting of solid catalyst particles, attrited solid catalyst particles, and heavy by-products is withdrawn from a point below the packed section. A first portion of the liquid stream is recycled to the flash zone at a point below the point of withdrawal of the liquid stream and above the top of the packed section. Carboxylic acid is recovered from a second portion of the liquid stream.

INFORMATION DISCLOSURE

Methods of production of acetic acid are described in the section entitled, "Acetic Acid and Derivatives," at pages 121 to 139 of Volume 1 of *Kirk-Othmer Encyclopedia of Chemical Technology*, Fourth Edition, published by John Wiley and Sons of New York in 1991.

U.S. Pat. No. 5,334,755 (Yoneda et al.) and U.S. Pat. No. 5,364,963 (Minami et al.) disclose processes for preparing acetic acid by carbonylation of methanol. One process uses a continuous flow stirred tank type reactor, and a portion of the solution in the reactor is withdrawn and fed through a line to a cooler, which cools that portion of the solution by indirect heat exchange with a cooling medium. The cooled solution is recycled to the reactor to maintain the temperature within the reactor at a predetermined range. Another process disclosed in U.S. Pat. Nos. 5,334,755 and 5,364,963 uses a plug flow type reactor that has a plurality of catalyst-containing pipes connected in parallel with each other. The reaction solution flows within the pipes. The pipes are surrounded by a sheath into which a cooling medium such as low temperature steam is supplied for indirect heat exchange. The heated steam may be used as a heat source for a distillation tower that recovers the acetic acid product.

U.S. Pat. No. 5,364,963 (Minami et al.) discloses a heterogeneous methanol carbonylation catalyst that includes a rhodium complex supported on a porous, cross-linked vinylpyridine resin, wherein the vinylpyridine resin has a cross-linking degree of 30–60%, a pore volume of 0.1–0.4 ml/g, and an average pore diameter of 20–100 nanometers (nm). The teachings of U.S. Pat. No. 5,364,963 that relate to the methanol carbonylation catalyst are incorporated herein by reference. U.S. Pat. No. 5,364,963, and U.S. Pat. No. 5,334,755 (Yoneda et al.) teach passing a portion of the effluent from a reactor containing such a catalyst to a distillation tower.

U.S. Pat. No. 5,663,430 (Morris et al.) discloses a methanol carbonylation process that uses a soluble iridium and/or rhodium homogeneous catalyst, with an alkyl halide promoter and an optional co-promoter, wherein the effluent of the carbonylation reactor passes to a flash separation vessel with a scrubbing section with a liquid wash.

U.S. Pat. No. 5,662,780 (Sasaki et al.) discloses an extraction method for purifying an aqueous solution of acetic acid that uses isopropyl acetate as the extracting medium.

U.S. Pat. No. 5,520,890 (Lorentzen, et al.) describes a multi-phase catalytic reactor in which a liquid product is separated from a slurry phase which contains a finely divided solid catalyst in a liquid medium.

U.S. Pat. No. 5,374,774 (Ochiai) describes a control system to control the liquid levels in a reactor-flasher combination used for the carbonylation of methanol to acetic acid using a homogeneous catalyst.

Figure 1:
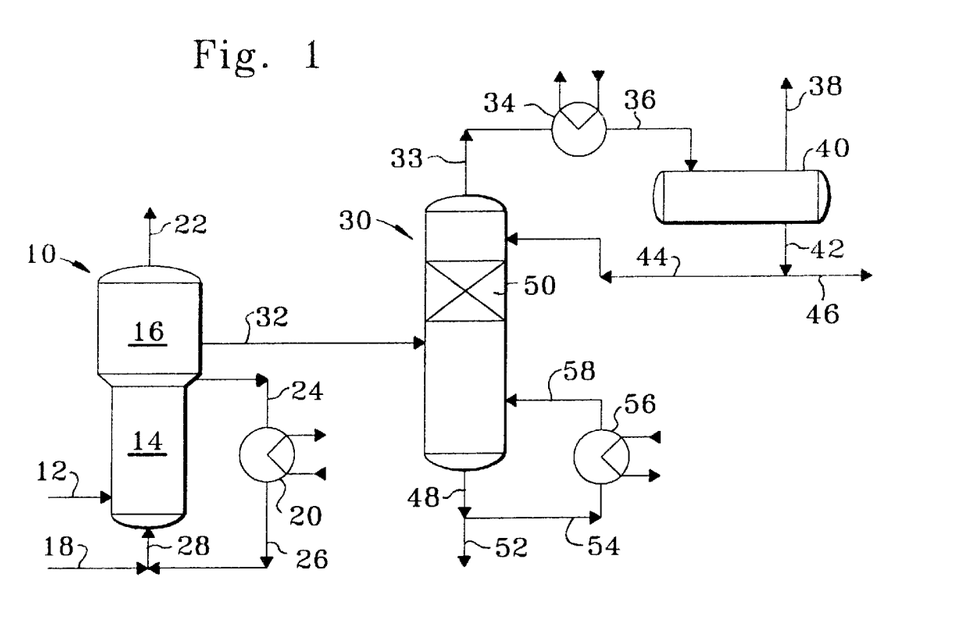
FIG. 1 shows a flow diagram of an embodiment of the invention.

European Patent Application EP-O-846674-A1 discloses a carbonylation process using a homogeneous catalyst for the production of a carboxylic acid that uses two reaction zones and a flash tank with a demister. FIG. 1 of EP-O-846674 shows an optional wash to the flash tank.

The paper entitled "The Chiyoda/UOP Acetica™ Process: A Novel Acetic Acid Technology," by Noriyuki Yoneda et al., which was distributed in association with the Third Annual Tokyo Conference on Advanced Catalytic Science and Technology" held in Tokyo, Japan, on Jul. 19–24, 1998, describes a process for producing acetic acid using a heterogeneous catalyst wherein the carbonylation reactor effluent liquid product is sent to a flash column to remove the crude acetic acid product and reject the carbon monoxide dissolved in the liquid.

U.S. Pat. No. 5,227,520 (Cooper) discloses a process for producing carboxylic acids in which the carbonylation reactor effluent passes to a preliminary flash vaporizer.

PEP Review No. 88-34 entitled "Acetic Acid by Low Pressure Carbonylation of Methanol with a Supported Rhodium Catalyst," by Wing S. Fong, in Process Economics Program, pp. 1–14, published by SRI International, Menlo Park, Calif., February 1990, describes a process for producing acetic acid using a heterogeneous-supported rhodium catalyst wherein the crude liquid product stream form the carbonylation reactor is flashed in a flash drum. The flashed vapors, containing acetic acid, water, methyl iodide, formic acid, and propionic acid pass to the purification section of the plant. After a small portion is bled off for catalyst regeneration, the slurry is recycled to the carbonylation reactor.

U.S. Pat. No. 3,769,329 (Paulik et al.) describes a process for the production of acetic acid from methanol in a liquid reaction medium using a homogeneous catalyst consisting essentially of a rhodium compound and a halogen component. The liquid effluent from the reactor passes through a pressure let down valve and is introduced into a distillation or flash column.

U.S. Pat. No. 3,791,935 (Eubanks et al.) describes a process for the purification of carboxylic acid using a homogeneous catalyst, wherein a stream of carboxylic acid to be purified, in either liquid or vapor form, is introduced into a packed, plate, or packed-plate distillation column. The distillation column has provisions for recycle of a portion of the column overhead stream to serve as reflux in the column.

DETAILED DESCRIPTION OF THE INVENTION

The most widely practiced process to which the present invention is applicable is the production of carboxylic acids by carbonylation. The carboxylic acids that can be produced by this invention are carboxylic acids having generally from 2 to 11, preferably from 2 to 6, and more preferably from 2 to 3, carbon atoms. The most preferable carboxylic acid is acetic acid. In addition to being applicable to processes that produce acetic acid primarily or solely, it is believed that this invention is also applicable to processes that co-produce acetic acid and acetic anhydride, as well as to processes that produce acetic anhydride primarily or solely.

The two feeds of this invention are (i) carbon monoxide and (ii) an alkyl alcohol and/or a reactive derivative of such an alkyl alcohol. Suitable alkyl alcohols include secondary alkyl alcohols, but primary alkyl alcohols are preferred. The alkyl alcohol has one fewer carbon atom than that of the desired carboxylic acid product, and accordingly the alkyl alcohol has generally from 1 to 10, preferably from 1 to 5, more preferably from 1 to 2, and most preferably 1 carbon atom. Among the suitable reactive derivatives of the alkyl alcohol are the alkyl halide derivative that corresponds to replacing the hydroxyl group of the alkyl alcohol with a halogen atom; the ether derivative that corresponds to replacing the hydrogen atom of the hydroxyl group of the alkyl alcohol with the alkyl group of the alkyl alcohol; and the ester derivative that corresponds to replacing the hydrogen atom of the hydroxyl group of the alkyl alcohol with the acetate group of the desired carboxylic acid product. In the production of acetic acid, the preferred alkyl alcohol and reactive derivative thereof are methanol and methyl acetate, respectively.

This invention is broadly applicable to any heterogeneous catalyst, and is not limited to any particular heterogeneous catalyst. Among heterogeneous catalysts, this invention is especially applicable to heterogeneous catalysts comprising a resin, in particular a resin having a strongly coordinating basic nitrogen. Resins having a strongly coordinated basic nitrogen include polymers having pendant quaternized N-base or alkylated N-oxide pyridine groups. The teachings of U.S. Pat. No. 5,360,929 with respect to quaternized N-base or alkylated N-oxide pyridine groups is incorporated herein by reference. Three preferred examples of these polymers are poly(2-vinylpyridine), poly(4-vinylpyridine), and poly(vinylpyrrolidone). The resin can also be a copolymer of two or more polymers having pendant quaternized N-base or alkylated N-oxide pyridine groups, such as a copolymer of poly(2-vinylpyridine) and poly(4-vinylpyridine); a copolymer of poly(4-vinylpyridine) and poly(vinylpyrrolidone); and a copolymer of poly(2-vinylpyridine), poly(4-vinylpyridine), and poly(vinylpyrrolidone). In addition, the resin can be a copolymer of polymers having pendant quaternized N-base or alkylated N-oxide pyridine groups and other polymeric building blocks, as exemplified by poly(4-vinylpyridine-co-butyl methacrylate), poly(2-vinylpyridine-co-styrene), poly(4-vinylpyridine-co-styrene), poly(1-vinylpyrrolidone-co-acrylic acid), quaternized poly(1-vinylpyrrolidone-co-2-dimethylaminoethyl methacrylate), and poly(1-vinylpyrrolidone-co-vinyl acetate). Suitable heterogeneous catalysts for use in this invention are disclosed in U.S. Pat. Nos. 4,328,125 (Drago et al.); U.S. Pat. No. 5,155,261 (Marston et al.); and U.S. Pat. No. 5,334,755 (Yoneda et al.); U.S. Pat. No. 5,364,963 (Minami et al.); and U.S. Pat. No. 5,466,874 (Scates et al.).

The preferred catalyst for use in this invention comprises a rhodium complex supported on a porous, cross-linked vinylpyridine resin. It is important that the vinylpyridine resin have a cross-linking degree of 30–60%, preferably 35–60%, a pore volume of 0.2–0.4 cc/g, preferably 0.25–0.4 cc/g, and an average pore diameter of 20–100 nm, preferably 30–90 nm. This catalyst has an improved catalyst life and exhibits high mechanical strengths (e.g. resistance to abrasion and crushing) and high catalytic activity.

When the cross-linking degree of the cross-linked vinylpyridine resin (hereinafter referred to as VP resin for brevity) is less than 30%, the pyridine is apt to be eliminated from the catalyst during use and the abrasion resistance of the catalyst is lowered. Too high a cross-linking degree in excess of 60% is disadvantageous because the catalyst activity is lowered. A pore volume of at least 0.2 cc/g is required for obtaining a desired catalytic activity. When the pore volume exceeds 0.4 cc/g, lowering of the abrasion resistance results. An average pore diameter less than 20 nm causes reduction of the catalytic activity, while an average pore diameter in excess of 100 nm causes the reduction of abrasion resistance.

It is useful at this point to define three additional terms that are used herein. The term "cross-linking degree" herein is defined as follows:

$$\text{Cross-linking degree } (\%) = (A/B) \times 100$$

wherein A represents the weight of the cross-linking agent contained in the VP resin and B represents the weight of the vinylpyridine monomer units of the VP resin.

The "pore volume" of the VP resin is measured by the mercury penetration method using Mercury Pressure Porosimeter Model 70 (manufactured by Carlo Elba Inc., Italy) with a mercury surface tension of 474 dyne/cm at 25° C., a contact angle of 140 degrees, and an absolute mercury pressure varying from 1 to 200 kg/cm$^2$.

The term "average pore diameter" used herein is defined as follows:

$$\text{Average pore volume } (nm) = 4(C/D) \times 10^3$$

wherein C represents the pore volume (cc/g) of the VP resin and D represents the surface area (m$^2$/g) of the VP resin measured by the B.E.T. method.

The VP resin may be produced by copolymerizing a vinylpyridine monomer with an aromatic compound having two vinyl groups as a cross-linking agent. The copolymerization method is well known in the art and may be, for example, a method in which a precipitant is added, a method in which a linear polymer is added, a method in which a swelling agent and a precipitant are added, and a method in which a diluent and a linear polymer are added. The method disclosed in Japanese Published Examined Patent Application No. 61-25731 may be particularly suitably used. In this method, a mixture containing a vinyl pyridine monomer, a cross-linking agent having two vinyl groups and, optionally, a vinyl monomer is reacted in the presence of a radical polymerization catalyst, a suspension stabilizing agent, and a precipitant using an aqueous suspension polymerization technique. The stabilizer may be a water-soluble polymer such as polyvinyl alcohol, hydroxyethyl cellulose, carboxymethyl cellulose, sodium polymethacrylate, sodium polyacrylate, starch, gelatin, or an ammonium salt of styrene/meleic anhydride copolymer, or an inorganic salt such as calcium carbonate, calcium sulfate, bentonite or magnesium silicate. The precipitant is an organic liquid which serves to function as a good solvent for the monomer but as a poor solvent for the copolymer produced. Examples of the precipitant include hydrocarbons having 5–10 carbon atoms such as isooctane, alcohols, and esters. The polymerization degree of the VP resin may be controlled by control of the amount of the cross-linking agent. The pore volume and the average pore diameter may be controlled by selection of the kind and amount of the precipitant. Suitable selection of the kind and amount of the suspension stabilizer and the reaction temperature is also effective to control the pore characteristics of the VP resin.

Illustrative of suitable vinylpyridine monomers for the production of the VP resin are 4-vinylpyridine, 2-vinylpyridine and 2- and 4-vinylpyridine derivatives having a lower alkyl group such as a methyl group or ethyl group on the pyridine ring. The vinylpyridine monomer may be used in conjunction with an aromatic vinyl monomer such as styrene or vinyltoluene. Such a vinyl monomer is used in an amount of 30 mole % or less, preferably 20 mole % or less, based on the total mole of total monomers. Illustrative of suitable cross-linking agents are aromatic divinyl compounds such as divinylbenzene and divinyltoluene and aliphatic divinyl compounds such as butadiene. The amount of the cross-linking agent is determined according to the intended cross-linking degree.

The VP resin is generally used in the form of beads, preferably spheres, having a particle size of 0.01–4 mm, preferably 0.1–2 mm, more preferably 0.4–2 mm. The VP resin is loaded with a rhodium complex $[Rh(CO)_2I_2]$ in any suitable manner. The amount of the rhodium complex loaded on the VP resin is 0.2–2% by weight, preferably 0.5–1.0% by weight, in terms of elemental rhodium, based on the weight of the VP resin.

The loading of the VP resin with the rhodium complex may be performed by contacting the VP resin with a rhodium salt in a solvent containing an alkyl iodide under a pressure of carbon monoxide. This method may be carried out by contacting the rhodium salt with the VP resin under conditions as generally adopted in the catalytic carbonylation of methanol. During the course of the above reaction, the pyridine ring of the VP resin are quaternized with the alkyl iodide to form a pyridinium salt to which is ionically bonded a rhodium carbonyl complex $[Rh(CO)_2I_2]$ formed by reaction of the rhodium salt, alkyl iodide and carbon monoxide.

Examples of the rhodium salts include rhodium halides such as rhodium chloride, rhodium bromide, and rhodium iodide. Illustrative of suitable alkyl iodides are lower alkyl iodides such as methyl iodide, ethyl iodide, and propyl iodide. The use of methyl iodide is preferred. The alkyl iodide is used in an amount of 2–2000 moles, preferably 5–500 moles, per mole of the rhodium salt. The carbon monoxide pressure under which the rhodium salt is contacted with the VP resin in the presence of the alkyl iodide is 7–30 kg/cm$^2$(g) (100–427 psi(g)), preferably 10–20 kg/cm$^2$(g) (142–284 psi(g)).

The loading of the VP resin with the rhodium complex is preferably performed by a method which includes the steps of:

(a) contacting a solid, pyridine ring-containing resin with an aqueous solution containing rhodium ion so that the rhodium ion is bound to the resin; and (b) contacting said rhodium ion-carrying resin with carbon monoxide and an alkyl iodide in an organic solvent so that the rhodium ion is converted to a rhodium complex bound to the resin.

This method of loading rhodium on the VP resin is also applicable to the production of conventional supported rhodium catalysts. Thus, any known VP resin can be also loaded with the rhodium complex using the method.

In the method to load rhodium on the VP resin, the VP resin is first contacted with an aqueous solution containing rhodium ions so that the rhodium ions are bound to pyridine rings of the resin. The aqueous solution may be prepared by dissolving a water soluble rhodium salt, such as rhodium chloride, rhodium bromide, or rhodium iodide, and preferably has a rhodium concentration of 1000–5000 ppm by weight, more preferably 1500–4000 ppm by weight, in terms of elemental rhodium. The contact of the resin with the aqueous solution may be performed, for example, by immersing the resin in the solution or by passing the solution through a column packed with the resin at a temperature of generally 20°–70° C. (68°–158° F.), preferably 25°–50° C. (77°–122° F.), for a period of time so that desirably 0.2–2% by weight of rhodium ions in terms of elemental rhodium is bound to the resin.

The resin to which rhodium ions have been bound is then contacted with an alkyl iodide and carbon monoxide in an organic solvent so that the rhodium ion bound to the pyridine ring is converted into rhodium complex bound to the pyridinium nitrogen quaternized by reaction with the alkyl iodide.

The alkyl iodide, which is preferably methyl iodide, is used in an amount of generally 2–2000 moles, preferably 50–500 moles, per mole of the rhodium ions bound to the resin. As the organic solvent, there may be used alcohols such an methanol, ethanol, and propanol; carboxylic acids such as acetic acid and propionic acid; esters such as methyl acetate, ethyl acetate, and methyl propionate; and dialkyl ethers such as dimethyl ether. The organic solvent may contain up to 10% by weight of water. The amount of the rhodium ion-carrying resin is generally 2–25% by weight, preferably 5–10% by weight, based on the weight of the organic solvent. The above reaction is generally performed at a temperature of 140°–250° C. (284°–482° F.), preferably 160°–220° C. (320°–428° F.) under a partial pressure of carbon monoxide of generally 5–30 kg/cm$^2$(g) (71–427 psi(g)), preferably 10–25 kg/cm$^2$(g) (142–356 psi(g)). The thus obtained rhodium complex loaded resin may be used as such for carbonylation of an alcohol but, if desired, may be separated from the reaction solvent and washed with an organic solvent such as methanol or acetic acid.

In the above method, the VP resin is first contacted with an aqueous solution containing rhodium cation to capture the rhodium cation. Since a rhodium salt is highly soluble in water, no rhodium salt precipitates through this first step. The aqueous solution after contact with the VP resin which still contains unbound rhodium cation can be reused after being added with a supplemental amount of the rhodium salt for adjusting the rhodium concentration. Therefore, all of the rhodium salt can be effectively utilized without loss. In the second step, the rhodium ion-carrying VP resin is reacted with an alkyl iodide and carbon monoxide in an organic solvent. Since the rhodium ion is ionically bound to the pyridine ring of the VP resin, no precipitates of rhodium salt are formed in the organic solvent during the course of the second step.

This preferred catalyst is disclosed in U.S. Pat. No. 5,364,963 (Minami et al.) and is available from Koei Chemical Industry Company, of Japan.

The thus prepared catalyst is advantageously used for the carbonylation of a lower alcohol, especially methanol. Acetic acid is produced by a process which comprises reacting carbon monoxide with methanol under a carbon monoxide pressure in the presence of an alkyl iodide and the above catalyst.

The carbonylation of methanol using the above heterogeneous catalyst may be carried out using any desired reactor, such as a fixed bed reactor, an expansion bed reactor, or a stirred tank reactor. The catalyst is placed in the reactor in an amount of, generally, 2–40% by weight based on the weight of the reaction solution contained therein, though the amount varies with the kind of the reactor used. It is recommendable to use the catalyst in an amount of 2–25% by weight in the case of a mixing type reactor, 20–40% by weight in the case of a fixed bed reactor, and 2–25% by weight in the case of an expansion bed reactor, based on the reaction solution contained therein.

As the reaction solution, a carbonyl group-containing compound having at least two carbon atoms is suitably used. Such a compound may be, for example, a saturated aliphatic acid such as acetic acid, propionic acid or butyric acid, an ester such as methyl acetate or ethyl acetate, an aromatic acid such as benzoic acid, or a mixture thereof. The reaction solution can contain up to 50% by weight, preferably 0.1–20% by weight of water. The alkyl iodide is preferably a lower alkyl iodide having 1–6 carbon atoms, such as methyl iodide.

It is preferred that the reaction solution within the reactor have a content of the carbonyl group-containing solvent of at least 0.30 part by weight per part by weight of the methanol present in the reaction solution within the reactor. By using such an organic solvent in such a specific amount, the catalyst can exhibit high catalytic activity and the dissociation of rhodium species from the polymer substrate can be minimized, so that the reaction can be performed at a low carbon monoxide partial pressure. Especially good results are obtainable with the use of the organic solvent in an amount of at least 2.4 parts by weight per part by weight of the methanol.

The term "the reaction solution within the reactor" used herein is intended to mean the solution which is present in the reactor at any point in time in the course of the reaction. Since methanol is consumed as the reaction proceeds, the relative amount of the solvent increases as the reaction proceeds. Thus, in the case of a batch type reactor, for example, the solution may be the raw material feed introduced into the reactor. In the case of a continuous flow, stirred tank-type reactor, the solution may be the product continuously discharged from the reactor. In the case of a piston flow type reactor, the solution may be the whole feed, inclusive of recycled solutions, to the reactor.

The methanol carbonylation is performed at a temperature of 140°–250° C. (284°–482° F.), preferably 160°–220° C. (320°–428° F.), and a carbon monoxide partial pressure of 7–30 kg/cm$^2$(g) (100–427 psi(g)), preferably 10–20 kg/cm$^2$(g) (142–284 psi(g)), while maintaining the total reaction pressure in the range of 15–60 kg/cm$^2$(g) (142–854 psi(g)), preferably 15–40 kg/cm$^2$(g) (213–569 psi(g)), more preferably 15–30 kg/cm$^2$(g) (213–427 psi(g)). The alkyl iodide, which is preferably methyl iodide, is used in an amount effective to promote the methanol carbonylation, generally in an amount of 1–40% by weight, preferably 5–30% by weight, based on the weight of the solution within the reactor. The rhodium loaded catalyst is used in a catalytically effective amount, generally in an amount of at least 50 ppm by weight, preferably at least 300 ppm by weight, more preferably at least 500 ppm by weight, in terms of elemental rhodium, based on the weight of the solution within the reactor.

The reaction zone for this invention may be a continuous stirred-tank reactor (CSTR). In a CSTR that uses a heterogeneous catalyst, a stirrer stirs the liquid and keeps the heterogeneous catalyst in suspension in the liquid, provided that the heterogeneous catalyst is finely divided. In addition, the reaction zone for this invention may be a slurry reactor. In a slurry reactor that uses a heterogeneous catalyst, the catalyst must again be finely divided. But in contrast to a CSTR, a slurry reactor is a gas-liquid-solid reactor in which the ascent of gas bubbles through the liquid keeps the heterogeneous catalyst in suspension in the liquid. Also, the reaction zone for this invention may be an ebullated-bed reactor that uses a heterogeneous catalyst. In an ebullated bed, as the term "ebullated bed" is used herein, liquid and gas flow co-currently and upwardly through the reactor, and it is the strong upflow of the liquid that serves to expand the heterogeneous catalyst bed, even though the bed as a whole does not move. The preferred reaction zone for this invention, however, is a three-phase transport reactor (3PTR). A 3PTR is similar to an ebullated bed reactor, except that the upflow of liquid is even stronger. In a 3PTR, the upflow of liquid entrains the heterogeneous catalyst and carries it out of the reactor. At the top of the 3PTR, gas is separated from the slurry of liquid and catalyst, which is recycled to the bottom of the 3PTR. A preferred 3PTR reactor for use in this invention is the reactor disclosed in U.S. Pat. No. 5,536,864 (Paret et al.) when operated with a heterogeneous catalyst. Because the 3PTR is the preferred reactor type, the description which follows will be directed mainly to a reaction zone that is a 3PTR, except where noted. CSTR's, slurry reactors, ebullated bed reactors, and 3PTR's are described in Chapter 9 of the book entitled *Catalytic Reactor Design,* by M. Orhan Tarhan, published by McGraw-Hill Book Company, New York, in 1983.

During the course of carbonylation reactions, the reaction effluent stream will inevitably contain a small content of solid catalyst particles. In addition, some of the solid catalyst particles will become attrited, either by mechanical attrition or by thermal attrition. Therefore, after a period of time in operation, the liquid stream that is withdrawn from a carbonylation reactor will contain not only the desired carboxylic acid product, but also solid catalyst particles and attrited solid catalyst particles. The solid catalyst particles and/or attrited catalyst particles, which are not dissolved in the reaction effluent stream, amount to less than about 2 wt-% of the reaction effluent stream. As the selectivity of the catalyst deteriorates, the reaction effluent stream may also contain heavy by-products.

This liquid stream, which exits from the separation section of a 3PTR, flows to a flash zone. Between the 3PTR and the flash zone, the stream generally undergoes a pressure reduction. This reduction in pressure vaporizes some of the liquid stream into a gas, thereby cooling the liquid stream. The pressure reductions can occur in one or more stages. Likewise, the flashing can occur in one or more stages. Thus, it is within the scope of this invention that the stream flowing from the separation zone passes serially through a train of pairs of pressure reductions and flashes.

The magnitude of the pressure reduction, and of the resultant temperature decrease, depends on a number of factors, including the desired carboxylic acid product, the temperature and pressure in the carbonylation reaction zone, and the composition of the liquid stream flowing from the reaction zone to the flash zone. For acetic acid production, the carbonylation reaction zone generally operates at a temperature of from about 150 to about 220° C. (302° to 428° F.) and at a pressure of generally from about 25 to about 60 kg/cm$^2$(g) (356 to 853 psi(g)), and preferably about 35 to about 45 kg/cm$^2$(g) (498 to 640 psi(g)), while the flash zone operates at a pressure of generally from about 0 to about 7 kg/cm$^2$(g) (0 to 100 psi(g)), and preferably about 0 to about 3.5 kg/cm$^2$(g) (0 to 50 psi(g)). For the production of other carboxylic acids, persons of ordinary skill in the art are able to compute the resultant decrease in temperature that occurs for a particular liquid stream composition as a result of a given pressure reduction between the reaction and flash zones.

The temperature of the flash zone is generally less than the temperature at which rapid thermal attrition of the solid catalyst particles occurs. Thus, the maximum temperature of the flash zone depends on several factors, including the susceptibility of the solid catalyst to attrit thermally, as well as the ability or inclination of the owner or operator of a carbonylation process to deal with a given rate of thermal attrition. However, it is believed that, for solid catalyst particles comprising resins such as polyvinylpyridine and polyvinylpyrrolidone, the maximum temperature of the flash zone is generally less than about 220° C. (428° F.), preferably less than about 200° C. (392° F.), and more preferably less than about 180° C. (356° F.). For the production of acetic acid, the flash zone preferably operates at a temperature of from about 105 to about 165° C. (221° to 329° F.).

The pressure reduction of the liquid stream enroute to the flash zone facilitates the separation of the entering liquid components from the solid catalyst particles. In general, the greater the reduction in pressure between the reaction zone and the flash zone, the greater is the resultant degree of separation between the liquids and solids in the flash zone. Although in theory operating the flash zone at a subatmospheric pressure would further improve the extent of liquid-solid separation, capital expenses, operating expenses, and practical complications associated with operating the flash zone at a vacuum far outweigh the benefits of a further decrease in the temperature of the liquid stream.

In general, the flash zone may be any suitable device for separation of liquids from solid catalyst particles. In its simplest form, the flash zone may be an empty vessel in which liquid and vapors, which are both entrained and a result of the pressure reduction, separate subject to the momentum of the entering liquid stream and under the force of gravity. However, to facilitate the separation, the flash zone preferably uses a packed section located between the inlet nozzle and the vapor outlet nozzle.

Although not a requirement of this invention, it is preferred that the flash zone comprise a packed section. The packed section performs two functions. First, the packed section provides a surface to intercept the attrited solid catalyst particles, including catalyst chips and fines, and heavy by-products that are carried upward with the gaseous or vaporous components toward the vapor outlet of the flash zone. Second, the packed section provides a surface that a hereinafter described liquid wash stream can irrigate in order to flush the attrited solid catalyst particles and heavy by-products downward toward the solid outlet of the flash drum. Generally at least 95 wt-%, and preferably at least 99.9 wt-% of the attrited solid catalyst particles and heavy by-products that enter the flash zone are captured and exit the flash zone through the solids outlet, rather than through a liquid or vapor outlet. If the flash zone comprises an empty vessel or drum, the inside surface of the a vessel wall intercepts attrited solid catalyst particles and heavy by-products, and the surface is irrigated by the wash stream, the available surface of the inner wall alone is generally insufficient to capture and remove much of these components. In addition, without packing, only a relatively small proportion of the upflowing components would even contact the wall, while the bulk of the components would flow upward through the middle of the drum vessel.

The packed section contains any suitable packing which may be one or more dumped packings and/or one or more arranged or structured packings. Suitable dumped packings include rings (i.e., Raschig or pall) and saddles (i.e., berl or intalox), and suitable arranged packings include Flexipac (known also as Mellapak) which is formed from lamellar or corrugated sheet metal. The packing material can be metallic, ceramic, or glass. Packed towers and packings are well known to persons of ordinary skill in the art of chemical engineering. A general description of packed columns is at pages 18–19 to 18–41 in *Perry's Chemical Engineers' Handbook,* 6th Edition, edited by R. H. Perry et al., published by McGraw-Hill Book Company, New York, in 1984.

The liquid wash stream that is introduced to the packed section to irrigate the packing is generally at least partially in the liquid phase, preferably at least 50 wt-% in the liquid phase, and more preferably at least 90 wt-% in the liquid phase. The stream preferably comprises the desired carboxylic acid product. More preferably, any stream in the process that has a concentration of the desired carboxylic acid product that is not less than that of the net overhead liquid stream from the flash zone may be used as the liquid wash stream. Where the flash zone produces more than one net overhead liquid stream, the concentration of the desired carboxylic acid product in the liquid wash stream is preferably not less than that of the net overhead liquid stream having the lowest concentration of the desired carboxylic acid. Preferably, the liquid wash stream contains water. In the production of acetic acid, if the flash zone produces a liquid crude acetic acid stream, a portion of the liquid crude acetic acid stream may be used for the liquid wash stream. In addition, if the liquid crude acetic acid stream is passed to downstream product recovery facilities, such as to a dehydration zone for water removal, and the dehydration zone produces a liquid refined acetic acid stream that has a higher acetic acid purity than the liquid crude acetic acid stream, then the liquid refined acetic acid stream may also be used as the liquid wash stream.

The flash zone may or may not have a reboiler, for it is not a requirement of this invention that the flash zone have a reboiler. However, it is preferred that the flash zone has a reboiler, and in such a case it is within the scope of one embodiment of this invention that the reaction medium or the reaction solution exchanges heat in the reboiler and thus provides some or all of the heat required for reboiling the flash zone. Whether the flash zone has a reboiler depends on a number of factors, including the composition of the reaction solution, in particular the concentrations of alkyl iodide and/or of byproducts such as methyl acetate in the reaction solution. In the case of the production of acetic acid, the concentration in the reaction solution of methyl iodide is generally from about 5 to about 20 wt-%, typically from about 10 to about 15 wt-%, and preferably from about 13 to about 14 wt-%, of the reaction solution, and the concentration in the reaction solution of methyl acetate is generally from about 0.5 to about 30 wt-%, typically from about 1 to about 4 wt-%, and preferably from about 2 to about 4 wt-%, of the reaction solution. In some acetic acid processes, the concentration of methyl acetate in the reaction solution is between about 10 and about 25 wt-% of the reaction solution. In general, within these ranges of concentrations, the greater the concentration of methyl iodide, or of methyl acetate, the more practical it is for the flash zone to have a reboiler.

Other factors that determine whether the flash zone has a reboiler include the compositions and the flow rates of the external reflux to the flash zone, if any, and of the wash fluid to the flash zone. The flow rate of the wash fluid to the flash zone is influenced by a number of factors including the flow rates of liquid, gas, entrained solid catalyst particles, and entrained attrited solid catalyst particles entering the flash zone; the cross-sectional area of the flash zone; the surface area of the packing of the flash zone; the nature of the particles (i.e., their tackiness or adherence) entering the flash zone; and the wetting characteristics of any packing in the flash zone. The flow rate of the wash fluid is generally between about 1 and about 25 wt-%, and preferably between about 6 and about 14 wt-%, of the sum of the net draw of water and the net draw of acetic acid from the flash zone. For purposes of computing this flow rate of wash fluid, the net draw of water is computed by adding the water in each net stream withdrawn from the flash zone, and the net draw of acetic acid is computed by adding the acetic acid in each net stream withdrawn from the flash zone. The net draw of water, or the net draw of acetic acid, may be withdrawn via more than one stream.

Figure 2:
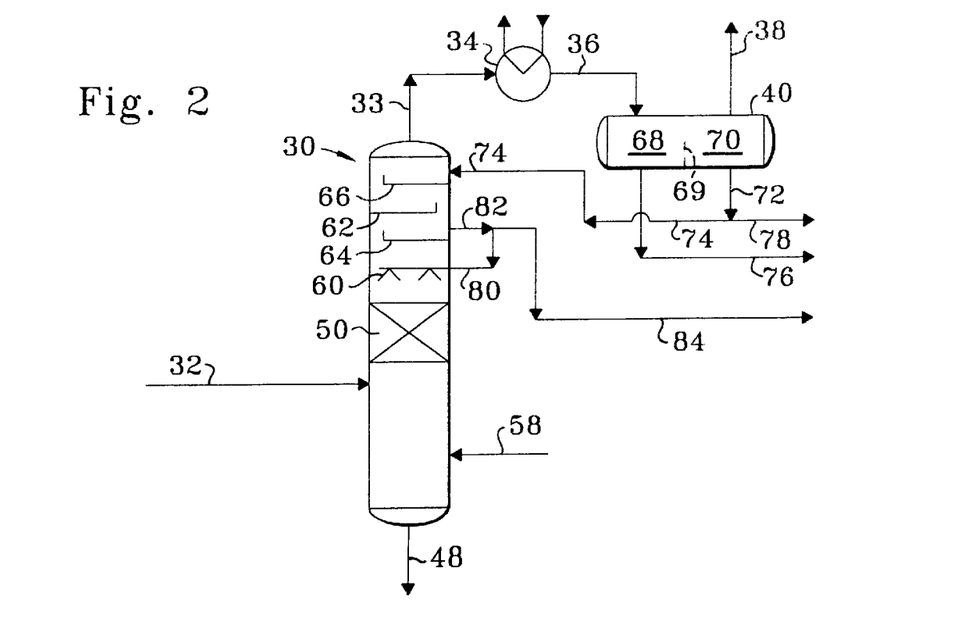
FIG. 2 depicts a flow diagram of another embodiment of the invention.

FIGS. 1 and 2 will now be used in describing two specific embodiments of the invention. The most widely practiced carbonylation process to which the present invention is applicable is the carbonylation of methanol with carbon monoxide to produce acetic acid. Therefore, the Figures will be described in terms of their application to an acetic acid production process. It is not intended that this description or these embodiments limit the broad scope of the invention as presented in the claims. The Figures show only elements and equipment which are essential to a clear understanding of the invention.

FIG. 1 illustrates a carbonylation 3PTR, which is generally denoted as 10, with a lower reaction section 14 and an upper separation section 16. A feed stream containing methanol in the liquid phase enters the process through a line 18 and combines with a recycle slurry stream flowing through a line 26. The recycle slurry stream contains solid catalyst particles and the reaction solution in the catalyst particle pores and in the interstitial volume between the catalyst particles. The combined stream of methanol and recycled slurry passes through a line 28 and enters the reaction section 14 of the reactor 10. A feed stream containing carbon monoxide in the gas phase also enters reactor 10 through a line 12. In the reaction section 14, carbon monoxide, which is provided in a molar excess, reacts with methanol to produce acetic acid via carbonylation in the presence of the catalyst particles while the gas-liquid-solid reaction medium is transported upward in the 3PTR. As used herein, the term "reaction medium within the reactor" used herein is intended to mean the combination of reaction solution and catalyst particles which is present in the reactor at any point in time in the course of the reaction. The reaction medium generally comprises carbon monoxide, methanol, acetic acid, and solid catalyst particles. In addition, the reaction medium may contain a catalytic promoter, such as an alkyl halide like methyl iodide, which is necessary for some solid catalyst particles. The reaction medium may also contain side reaction by-products such as water and methyl acetate. The presence of methyl acetate can be explained as the corresponding ester that results from the esterification of the alcohol and the product acetic acid. Heavy by-products of side reactions, such as propionic acid and acids having 3 or more carbon atoms, may also be present. Propionic acid can, in turn, react with methanol by esterification to form methyl propionate, another heavy by-product. Thus, the reaction medium can contain not only esters which have a boiling point less than that of acetic acid, such as methyl acetate, but also esters, such as methyl propionate, which have a boiling point greater than that of acetic acid.

At the top of the reaction section 14, the upflowing reaction medium enters the separation section 16 where the gas, liquid, and solid components of the reaction medium disengage to some extent. To aid disengagement, the separation section 16 generally has a larger cross-section than the reaction section 14 and contains baffles and other internal devices. Gaseous components such as unreacted carbon monoxide exit the separation section 16 through a line 22. These gaseous components can be recycled to the reaction section 14 by means not shown in FIG. 1. Liquids such as acetic acid, methyl acetate, methyl iodide, propionic acid, and any unreacted methanol, along with both soluble gases and entrained solid catalyst particles in the liquid, exit the separation section 16 through a line 32. A slurry of solid catalyst particles with entrained liquids and some soluble gases in the pores and in the interstitial volume exit through a line 24. At the conditions of reaction section 14, the carbonylation of methanol to acetic acid is an exothermic reaction. The exothermic heat of reaction, as computed form standard heats of formation at 25° C. (77° F.) of gaseous carbon monoxide, liquid methanol, and liquid acetic acid, is about 33 kcal/g-mole (137 kJ/g-mole). This heat of reaction is removed by cooling the slurry flowing through the line 24 in the cooler 20. Typically, the cooling medium is boiler feed water, which is vaporized to steam, which in turn can be used for heating elsewhere in the process. The cooled slurry flows through the line 26 and combines with the methanol feed stream in the line 18, as previously described.

The stream flowing through the line 32 is depressured and then enters a flash drum, which is generally denoted as 30. The pressure reduction of the liquid stream enroute to the flash drum 30 facilitates the separation of liquids and solid catalyst particles in the flash drum 30. The stream flowing through the line 32 generally contains less than 1 wt-% solids. On entering the flash drum 30, a portion of the stream flowing through the line 32 flows upward and into a packed section 50 of the flash drum 30. The packed section 50 is a counter-current contacting zone, in which upward flowing light components materials contact a downward flowing liquid in order to remove solid catalyst particles, attrited solid catalyst particles, and heavy by-products. The light materials are carried upward through the packed section 50, to the top of the flash drum 30, and through a line 33 include carbon monoxide, water vapor, methyl acetate, methyl iodide, acetic acid vapor, and any residual unreacted methanol. These upward flowing light materials carry solid catalyst particles, attrited solid catalyst particles, and heavy by-products, which are intercepted by the packing in the packed section 50 and are irrigated toward the bottom of the flash drum 30 by the downward flowing wash liquid.

Condenser 34 condenses most of the acetic acid, methyl iodide, methyl acetate, water, and any residual methanol in the stream flowing through the line 33. A two-phase vapor-liquid stream flows through a line 36 and enters a receiver 40. The receiver 40 is particularly well-suited for separating noncondensed components from a single liquid phase as opposed to from two liquid phases. Such a single liquid phase can be produced in the receiver 40 when the receiver conditions are such that the amount of condensed methanol and/or acetic acid in the receiver 40 is sufficient to solubilize in a single phase not only the water but also the methyl acetate and methyl iodide present in the receiver 40. Noncondensed components, such as carbon monoxide, exit the receiver 40 through a line 38, and can be recycled to the reaction section 14 by means not shown in FIG. 1. The condensed liquids exit the receiver 40 through a line 42. A portion of the condensed liquids is withdrawn through a line 46 and passed to further downstream separation facilities, which are not shown in FIG. 1. Such facilities are known to persons of ordinary skill in the art and do not require detailed description herein. These separation facilities can comprise means for recycling methyl acetate and methyl iodide to the reaction section 14, for rejecting water from the process, and for recovering acetic acid product.

Another portion of the condensed liquid flowing through the line 42 passes through a line 44 and enters the flash drum 30 at a point above the packed section 50. A distributor (not shown in FIG. 1) can be used to ensure that the condensed liquid is distributed uniformly across the entire cross-section of the packed section 50. The condensed liquid flows downward through the packing, and countercurrent to the upward flowing components described previously.

The liquid that exits the bottom of the packed section 50 contains the attrited solid catalyst particles and heavy by-products that were removed from the upflowing vapors. These liquids and solids leave the flash drum 30 through a line 48. The solids content of the stream flowing in the line 48 is generally less than 25 wt-%, and preferably less than 10 wt-%, in order to ensure that the stream becomes neither too solids-rich so as to foul and plug equipment nor too viscous so as to be unable to be pumped freely. A portion of the stream in the line 48 flows through a line 54, is heated in a heater 56, and passes to the flash drum 30 via a line 58. The heating medium for the heater 56 can be any suitable heating medium, such as steam. Another portion of the stream in the line 48 passes through a line 52 and is recycled to the reaction section 14 by means not shown in FIG. 1.

FIG. 2 illustrates an embodiment of the invention in which vapor-liquid contacting trays are located in the flash drum between the packing section and the vapor outlet, and there are two net liquid streams from the flash drum receiver. This is in contrast to FIG. 1, where there are no vapor-liquid contacting trays in the flash drum and where there is only one net liquid stream from the receiver. Despite this difference, the process depicted in FIG. 2 is very similar to the process depicted in FIG. 1, and consequently parts of FIG. 1 correspond directly to parts of FIG. 2. Corresponding parts in FIGS. 1 and 2 have been given the same reference numbers. Accordingly, in the process depicted in FIG. 2, lines 32, 48, and 58 interconnect with lines and equipment that are shown in FIG. 1 but which for the sake of brevity are not shown in FIG. 2. Likewise, in order to avoid repetitious description, the detailed description of FIG. 2 that follows does not repeat the previous detailed description of the parts of the process of FIG. 1 that are not shown in FIG. 2.

Referring now to FIG. 2, the light components, solid catalyst particles, attrited solid catalyst particles, and heavy by-products that enter the bottom of the packed section 50 in the flash drum 30 countercurrently contact a downflowing liquid wash stream comprising acetic acid. This liquid wash stream is produced using the previously mentioned vapor-liquid contacting trays located in the flash drum between the packing section 50 and the vapor outlet line 33. Three vapor-liquid trays, namely a top-most tray 66, an intermediate tray 62, and a bottom-most tray 64, are shown in FIG. 2. Thus, intermediate tray 62 schematically represents all the possible intermediate trays that may be located between the top-most tray 66 and the bottom-most tray 64, of which there may 10 or more intermediate trays.

Unlike FIG. 1 where the overhead vapor stream flowing through the line 33 contained a significant amount of acetic acid vapor along with water vapor, methyl acetate, methyl iodide, and any residual methanol vapor, in FIG. 2 the acetic acid is withdrawn as a liquid crude acetic acid stream via a line 82 from the bottom-most tray 64. A portion of the liquid crude acetic acid stream is recycled through a line 80 and a distributor 60 to a point above the packed section 50 in order to provide liquid wash to the packed section 50. The remaining portion of the liquid crude acetic acid stream, which may contain water, is routed through a line 84 to product recovery facilities, which are not shown in FIG. 2.

Thus, in FIG. 2, the line 33 carries a vapor stream comprising carbon monoxide, water vapor, methyl acetate, and methyl iodide vapor. A portion of each of water vapor, methyl acetate, and methyl iodide vapor in this vapor stream is partially condensed in condenser 34, and a vapor-liquid stream flows through a line 36 into a receiver 40. Receiver 40 has a baffle 69 which divides the receiver 40 into two compartments, 68 and 70. The receiver 40 is particularly well-suited for separating noncondensed components form two liquid phases as opposed to from a single liquid phase. Two liquid phases can form in the receiver 40 when the receiver conditions are such that the amount of condensed methanol and/or acetic acid in the receiver 40 is not sufficient to solubilize in a single phase all of the methyl acetate, methyl iodide, and water. Under these conditions, a water-rich phase comprising water, acetic acid, and trace amounts of methyl acetate and methyl iodide, and a water-poor phase comprising methyl acetate, methyl iodide, and trace amounts of water and acetic acid are formed. As used herein, the term water-rich means having a concentration of water of equal to or greater than 40 wt-% and water-poor means having a concentration of water of less than 40 wt-%.

In receiver 40, the vapor-liquid stream is separated into the water-poor phase in the compartment 68 and the water-rich phase in a compartment 70. The water-poor phase is withdrawn from the compartment 68 and flows through a line 76 to recovery facilities, also not shown in FIG. 2, so that a portion of the water-poor phase can be recycled to the reaction section 14. The water-rich phase is withdrawn from compartment 70 through a line 72. A portion of the water-rich phase is refluxed to the top-most tray 66 of the flash drum 30 via a line 74. The remainder of the water-rich phase flows through a line 78 to recovery facilities, not shown in FIG. 2, so that a portion of the water-rich phase can also be recycled to the reaction section 14. Carbon monoxide and the portion of the water vapor, methyl acetate, and methyl iodide that did not condense in the condenser 34 are recovered as a net vapor stream from receiver 40 through a line 38. This vapor stream also flows to recovery facilities, which are not shown in FIG. 2, in order to recycle at least the carbon monoxide to the reaction section 14.

What is claimed is:

1. A process for the production of a carboxylic acid, the process comprising the steps of:
   a) reacting (i) an alcohol and/or a reactive derivative of an alcohol and (ii) carbon monoxide in the presence of solid catalyst particles in a reaction zone to produce a carboxylic acid, and forming in the reaction zone a reaction effluent comprising (i) the carboxylic acid, (ii) carbon monoxide, and (iii) at least one of the solid catalyst particles, attrited solid catalyst particles, and heavy by-products;
   b) flashing at least a portion of the reaction effluent in a flash zone, and recovering from the flash zone an overhead fraction comprising the carboxylic acid;
   c) forming from the overhead fraction a vapor phase comprising carbon monoxide and an at least partial liquid phase comprising the carboxylic acid;
   d) separating the vapor phase and the at least partial liquid phase in an overhead receiver;
   e) recycling the at least partial liquid phase to the flash zone; and
   f) recovering a product comprising the carboxylic acid from the at least partial liquid phase.

2. The process of claim 1 further characterized in that the flash zone operates at a temperature of less than about 220° C.

3. The process of claim 1 wherein at least 50% by weight of the at least partial liquid phase is liquid.

4. The process of claim 1 further characterized in that the flashing of the reaction effluent in Step (b) comprises depositing at least one of the solid catalyst particles, the attrited solid catalyst particles, and the heavy by-products on a surface within the flash zone, and the recycling of the at least partial liquid phase in Step (e) comprises contacting at least a portion of the surface containing deposits of at least one of the solid catalyst particles, the attrited solid catalyst particles, and the heavy by-products with liquid and removing at least a portion of the deposits from the surface.

5. The process of claim 4 further characterized in that the flash zone comprises a vessel having an inner wall, and at least part of the surface comprises at least part of the inner wall.

6. The process of claim 4 further characterized in that the flash zone comprises a packed section containing packing, and at least part of the surface comprises at least part of the packing.

7. The process of claim 1 further characterized in that a bottom stream comprising at least one of the solid catalyst particles and the attrited solid catalyst particles is withdrawn from the flash zone, and at least a portion of the bottom stream is recycled to the reaction zone.

8. The process of claim 1 wherein the overhead fraction comprises at least one of the group consisting of carbon monoxide, an ester corresponding to the esterification of the alcohol and the carboxylic acid, and water.

9. The process of claim 1 wherein the solid catalyst particles comprise a polyvinylpyridine resin.

10. The process of claim 1 wherein the solid catalyst particles comprise a polyvinylpyrrolidone resin.

11. The process of claim 1 wherein the alcohol comprises methanol, and the carboxylic acid comprises acetic acid.

12. A process for the production of a carboxylic acid, the process comprising the steps of:
   a) reacting (i) an alcohol and/or a reactive derivative of an alcohol and (ii) carbon monoxide in the presence of solid catalyst particles in a reaction zone to produce a carboxylic acid, and forming in the reaction zone a reaction effluent comprising carbon monoxide, water, an ester corresponding to the esterification of the alcohol and the carboxylic acid, the carboxylic acid, and at least one of the group consisting of the solid catalyst particles, the attrited solid catalyst particles, and the heavy by-products;
   b) flashing the reaction effluent in a vertically-oriented flash zone, wherein the flash zone has a rectification section in an upper portion of the flash zone and a packed section in a lower portion of the flash zone and wherein the packed section contains packing, withdrawing from the flash zone at a point above the top of the rectification section a vapor fraction comprising carbon monoxide, water, and the ester, forming in the flash zone at a point below the top of the rectification section and above the top of the packed section a liquid fraction comprising the carboxylic acid, and withdrawing a bottom stream comprising the carboxylic acid and at least one of the group consisting of the solid catalyst particles, the attrited solid catalyst particles, and the heavy by-products from a point below the packed section;
   c) recycling the liquid fraction to a point below the point of formation of the liquid fraction and above the top of the packed section; and
   d) recovering a crude product comprising the carboxylic acid from the liquid fraction.

13. The process of claim 12 further characterized in that the flashing of the reaction effluent in Step (b) comprises depositing at least one of the solid catalyst particles, the attrited solid catalyst particles, and the heavy by-products on the packing within the packed section, and the recycling of the crude fraction in Step (c) comprises contacting at least a portion of the packing containing deposits of at least one of the solid catalyst particles, the attrited solid catalyst particles, and the heavy by-products with liquid and removing at least a portion of the deposits from the packing.

14. The process of claim 12 wherein the carboxylic acid comprises acetic acid and the ester comprises methyl acetate.

15. The process of claim 1 wherein the at least partial liquid phase comprises water.

16. The process of claim 12 wherein the solid catalyst particles comprise a polyvinylpyridine resin.

17. The process of claim 12 wherein the solid catalyst particles comprise a polyvinylpyrrolidone resin.

18. The process of claim 12 wherein the liquid fraction comprises water.

19. The process of claim 12 further characterized in that a vapor phase comprising carbon monoxide, a water-poor phase comprising the ester, and a water-rich phase comprising the ester are formed from the vapor fraction; the vapor phase, the water-poor phase, and the water-rich phase are separated in an overhead receiver; and the water-rich phase is recycled to the flash zone.

20. The process of claim 19 further characterized in that the water-rich phase is recycled to a point above the top of the rectification section.

21. The process of claim 19 further characterized in that the water-poor phase comprises methyl iodide.

* * * * *